United States Patent [19]

Spatz

[11] 3,989,716

[45] Nov. 2, 1976

[54] PYRRYLFLUORAN COMPOUNDS

[75] Inventor: Sydney M. Spatz, Circleville, Ohio

[73] Assignee: The Mead Corporation, Dayton, Ohio

[22] Filed: Apr. 29, 1975

[21] Appl. No.: 572,750

[52] U.S. Cl. .......................... 260/326.34; 260/335; 428/306; 428/307; 428/323; 428/325; 428/327; 282/27.5
[51] Int. Cl.[2] .................................... C07D 405/14
[58] Field of Search ............... 260/326.34, 326.14; 428/306, 307, 323, 327, 325; 282/27.5

[56] References Cited

UNITED STATES PATENTS

| 3,501,331 | 3/1970 | Kimura et al. | 428/307 |
|---|---|---|---|
| 3,514,310 | 5/1970 | Kimura et al. | 428/307 |
| 3,764,369 | 10/1973 | Hoover et al. | 428/307 X |
| 3,837,906 | 9/1974 | Jones | 428/325 |
| 3,930,672 | 1/1976 | Ozutsumi et al. | 428/323 |
| 3,936,564 | 2/1976 | Miyazawa et al. | 428/323 |

OTHER PUBLICATIONS

Hollins, *The Synthesis of Nitrogen Ring Compounds*, (1924), pp. 28–29.

*Primary Examiner*—R. Gallagher
*Assistant Examiner*—Mary C. Vaughn
*Attorney, Agent, or Firm*—Wilson G. Palmer; Stephen H. Cagle

[57] ABSTRACT

This invention discloses novel pyrrylfluoran compounds useful as the color-precursors or imaging sources in pressure-sensitive copy papers and in thermally-sensitive imaging papers, and a process for preparing these compounds which involves reacting under mild acid catalysis a mixture containing equimolar parts of a 2-amino-6-dialkylaminofluoran and a diketone taken from the group consisting of acetonylacetone, 2,5-heptanedione and 3,6-octanedione.

8 Claims, No Drawings

PYRRYLFLUORAN COMPOUNDS

BACKGROUND OF THE INVENTION

The present invention relates to novel pyrrylfluoran compounds which are colorless or essentially colorless, but are instantaneously colorable when brought into reactive contact with suitably sensitized sheets containing an acidic electron-acceptor such as the protic acids, e.g., organic acids, phenolic acids, phenols, diphenols, phenolic resins of the novolak type, and aprotic acids, e.g., Lewis acids, acid clays, etc., or mixtures of these materials. These properties and others disclosed hereinafter make the compounds of this invention suitable for use in various types of carbonless pressuresensitive copy papers, thermally-sensitive imaging papers, thermally-sensitive imaging transparencies for overhead projection screens and other copy or image applications.

A number of chemical compounds are disclosed in the prior art to be useful as color-precursors when brought into contact with acidic electron-acceptors. Included in the suitable compounds are the 2-amino-6-dialkylaminofluoran compounds the preparation of which and/or use in pressure sensitive papers are disclosed in U.S. Pat. Nos. 3,501,331; 3,624,107; 3,824,119; 3,825,561; and 3,839,361. Belgian Pat. No. 795,747 discloses 2-amino-6-dialkylaminofluoran compounds in which the 2-amino group is part of a fully reduced 5 or 6 membered heterocyclic ring such as pyrrolidine, piperidine, piperazine, morpholine and thiomorpholine.

STATEMENT OF THE INVENTION

In accordance with the present invention, novel pyrrylfluoran compounds are produced represented by generic Formula I

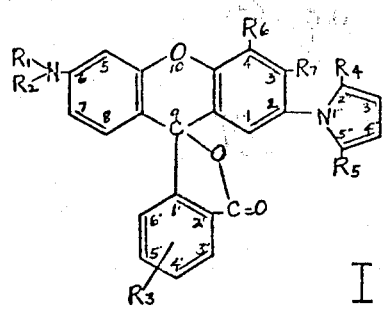

wherein, $R_1$ and $R_2$ may be same or different and each represents hydrogen or lower alkyl groups containing one to four carbon atoms, $R_3$ is hydrogen or a methyl group, $R_4$ and $R_5$ each represents a methyl or ethyl group, and $R_6$ and $R_7$ each represents hydrogen, a methyl or ethyl group or chlorine. The resultant fluoran compounds are colorless or substantially colorless compounds which in the presence of an acidic electron-acceptor are converted to resonance forms which are red in color.

In accordance with one feature of this invention, pressure-sensitive copying papers are produced having coated thereon microcapsules containing an organic solvent solution of the substantially colorless pyrrylfluoran compounds which in coming in contact with an electron-acceptor forms a colored dye.

According to another feature of this invention, novel pyrrylfluoran compounds are prepared by reacting under mild acid catalysis a mixture containing approximately equimolar parts of 2-amino-6-dialkylaminofluoran and a diketone taken from the group consisting of acetonylacetone, 2,5-heptanedione and 3,6-octanedione.

DETAILED DESCRIPTION OF THE INVENTION

The compounds of this invention prepared by the process of this invention and represented by generic Formula I are novel compounds. The structures of the compounds obtained by the reaction of this invention conform to the general structure represented by Formula I. This was established by elementary analyses and infrared spectroscopy. All of the infrared (IR) spectra showed a strong absorbance band at or near 1760 $cm^{-1}$, characteristic of the carbonyl group of the lactone ring. The found elementary analyses for carbon, hydrogen and nitrogen checked the calculated or theoretical values closely.

Solutions of these compounds, dissolved in organic solvents, such as benzene, acetone, ethanol or isopropylbiphenyl, produce strong to intense red colors when brought into contact with electron-acceptors, such as the previously described protic and aprotic acids. Thus, these color-precursors are useful as color-formers for pressure-sensitive copy papers, thermally-sensitive imaging papers and other copy or image applications. Furthermore, the images obtained from the color-precursors of this invention are readily copiable from electrostatic copy machines. Hence, in suitable admixture with blue and orange-producing precursors or with blue and green-producing precursors, the precursors, the precursors of this invention can yield deep-blue or blue-black, copiable images.

The essentially colorless color-precursors conforming to generic structure I yield red colors when brought into reactive contact with acidic electron-acceptors.

The colored dye structures formed by this invention may be represented by the cationic resonance extremes Formulae II and III.

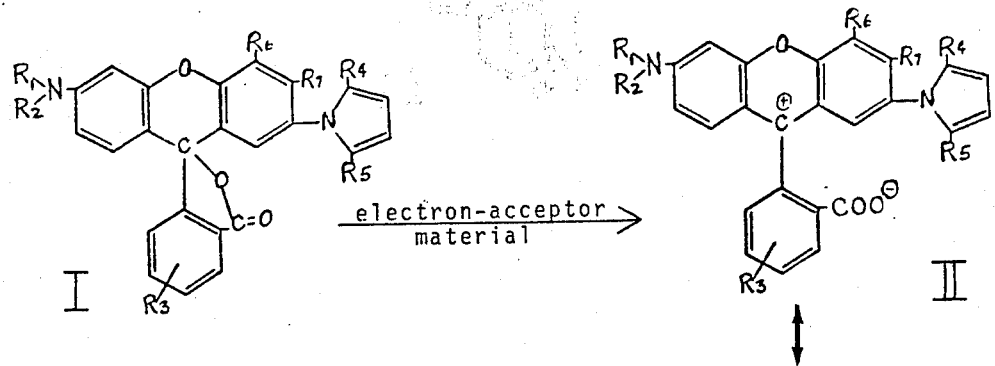

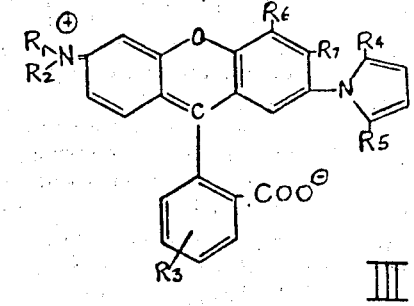

III

Typical of the pyrrylfluoran compounds produced by this invention are 6-diethylamino-2-(2'',5'''-dimethylpyrryl)fluoran, 6-dimethylamino-2-(2'',5'''-dimethylpyrryl)fluoran, 6-dimethylamino-2-(2'',5'''-dimethylpyrryl)4'-(or 5'')-methylfluoran, 6-diethylamino-2-(2'',5'''-dimethylpyrryl)-4-methylfluoran, 3-chloro-6-diethylamino-2-(2'',5'''-dimethylpyrryl)fluoran, 3-chloro-6-dipropylamino-2-(2'',5'''-dimethylpyrryl)fluoran, and 6-dibutylamino-2-(2'',5'''-dimethylpyrryl)fluoran.

The fluoran compounds of this invention may be dissolved in an organic solvent, such as chlorinated biphenyl, chlorinated biphenyl ether, isopropylbiphenyl or an alkylated naphthalene, microencapsulated in gelatin capsules, and the microcapsules may be coated on a paper substrate in the manner described in U.S. Pat. No. 2,712,507 to give a pressure-sensitive copying paper.

Generally, the process for making the novel compounds of This invention involves heating under mild acid catalysis a mixture containing approximately equimolar parts of the 2-amino-6-dialkylaminofluoran intermediate (Formula IV) with acetonylacetone or one of tis homologs (Formula V) wherein one or both of the ω-methyl groups are replaced by ethyl groups as for example, 2,5-heptanedione and 3,6-octanedione. The condensation reaction is as follows:

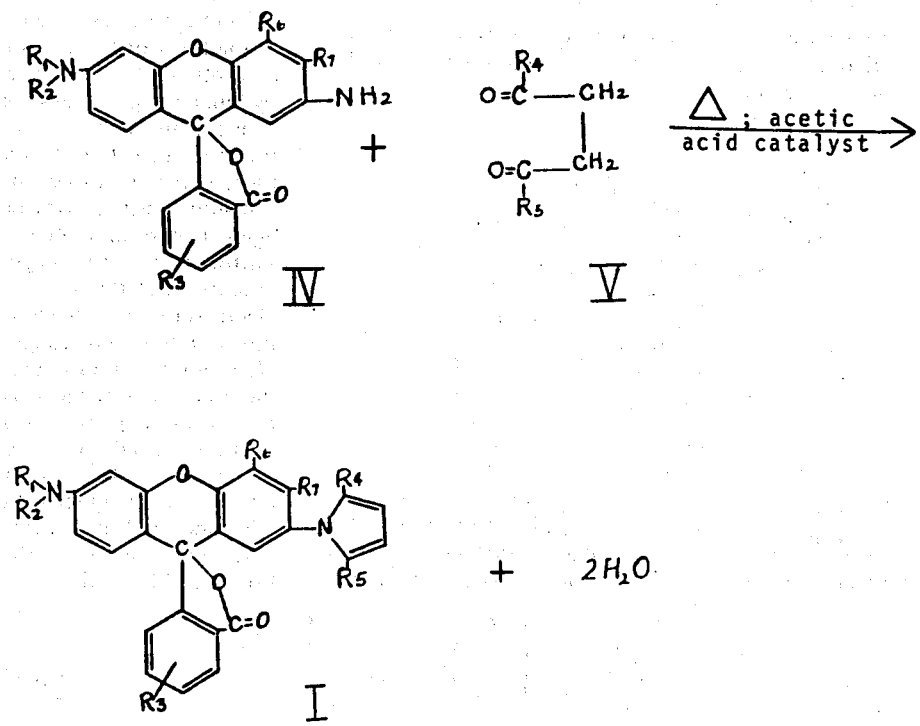

The reaction conditions, such as temperature, time and amount of acid catalyst are not critical. A wide range of temperature, say 40° to 120° C, may conveniently be used. However, if excess diketone is present a temperature up to the boiling point of the diketone may be used. A diluent, such as acetone, ethanol or propanol may be added to facilitate agitation during refluxing. The diluent should be a solvent for the desired pyrrylfluoran. If a diluent is present, the temperature should preferably be at the reflux temperature of the reaction mixture, say 60° to 90° C. Reaction time may be 1 to 24 hours preferably, at the preferred temperature range, may be 1.5 to 5 hours. The amount of acid catalyst may be from 1 to 15%, based on the weight of the reactants, of a mild acid, such as glacial acetic acid. The preferred range is 2 to 5% of the acid.

In place of acetic acid, acids such as propionic acid and other alkanoic acids having acid dissociation constants similar to that of acetic acid, as listed in any handbook of chemistry, may be used as catalysts in the reaction of Formula IV and Formula V to Formula I.

After the reaction period, the pyrrylfluoran compound may be recovered from the reaction product by cooling the mixture until precipitation is essentially complete, filtering the precipitate formed, washing the precipitate with methanol and drying. The yields of the compounds of Formula I have been of the order of 90% of theory.

A known process for preparing the compounds of intermediate IV, which represents a 2-amino-6-dialkylaminofluoran, comprises condensation in an acidic medium of essentially equimolar quantities of the starting materials represented by Formulae VI and VII. These materials may be reacted typically at 70°–95° C for 2 to 4 hours in concentrated sulfuric acid, followed by cooling, drowning in ice-water and bringing the reaction mix to pH 8 to 8.5 with ammonium hydroxide. These intermediates are isolated by filtration and purified by methods described hereinafter in Examples 3 and 5. The general condensation reaction is described in U.S. Pat. No. 3,839,361 and is illustrated as follows

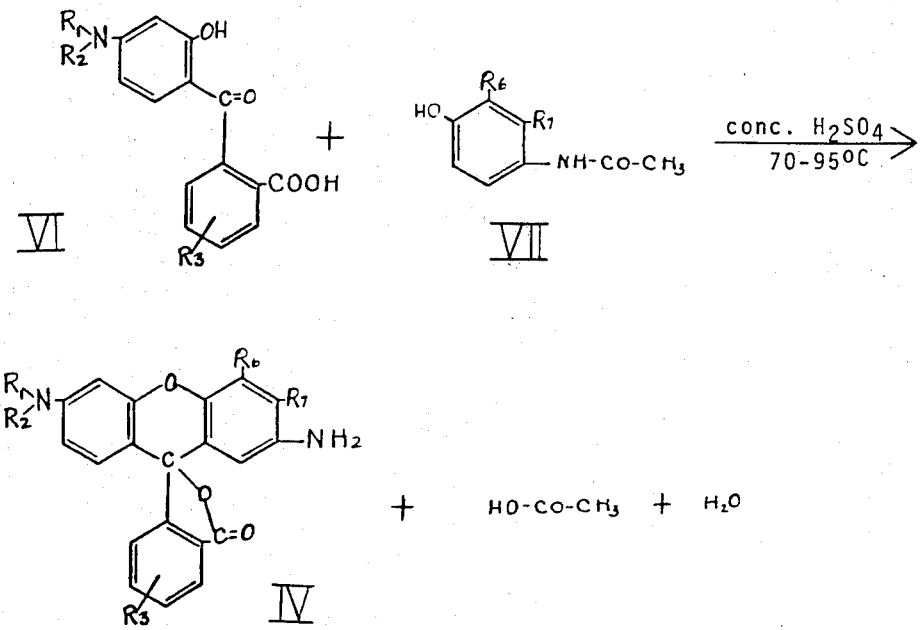

wherein $R_1$, $R_2$, $R_3$, $R_6$ and $R_7$ are the same as defined for generic Formula I.

Typical examples of Formula VI compounds are
2-(4'-N,N-dimethylamino-2'-hydroxybenzoyl)benzoic acid,
2-(4'-N,N-dimethylamino-2'-hydroxybenzoyl)benzoic acid,
2-(4'N,N-diethylamino-2'-hydroxybenzoyl)benzoic acid,
2-(4'-N,N-dimethylamino-2'-hydroxybenzoyl)-4-methylbenzoic acid, and
2-(4'-N,N-dibutylamino-2'-hydroxybenzoyl)benzoic acid.

These may be in turn prepared by known processes involving the condensation of phthalic anhydride or a substituted phthalic anhydride (Formula IX) with a m-dialkylaminophenol (Formula VIII). One such process is described in U.S. Pat. No. 3,501,331. The reaction is shown generically as follows.

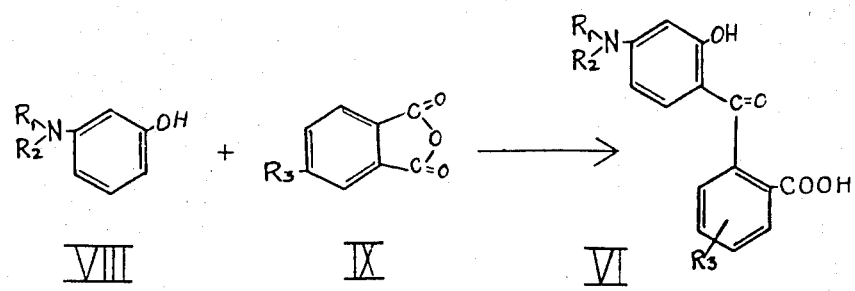

7

Typical examples of Formula VII compounds are 4-acetamidophenol and other 4-acetamidophenols containing a methyl, ethyl, or chlorine atom ortho or meta to the acetamido group.

The preferred embodiment of this invention is illustrated but not limited by the examples which follow.

EXAMPLE 1

Preparation of 2-amino-6-diethylaminofluoran intermediate

This intermediate was prepared according to Example B of U.S. Pat. 3,764,369 by the condensation of 2-(4'-diethylamino-2'-hydroxybenzoyl)benzoic acid at 80° C ±5° C for three hours. The yield of product, isolated and purified by the method used for Example 3, was 40.5% of theory. The melting point of the purified intermediate was 208°–212° C.

EXAMPLE 2

Preparation of 6-diethylamino-2-(2'',5''-dimethylpyrryl)fluoran (Formula X)-

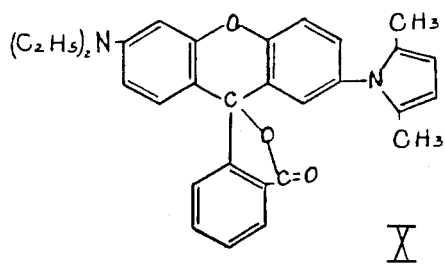

A mixture of 11.6 g. (0.03 mole) of 2-amino-6-diethylaminofluoran prepared in Example I and 3.59 g. (0.0305 mole) of 97% strength acetonylacetone in 30 ml. of anhydrous ethanol, containing 0.5 ml. of glacial acetic acid, was refluxed for 3.5 hours at 77°–79° C. Most of the reaction material dissolved within one hour. The reaction mix was cooled to room temperature under stirring, allowed to stir for several hours at room temprature, and finally in a refrigerator below 0° C for 45 minutes. The slurry of crystalline material was filtered on a small Buchner funnel. The yield of pale tan crystalline cake, after washing with cold methanol and drying to constant weight, was 12.72 g. (91.3% of theory). The melting point was 219–220° C. For the purpose of identifying and characterizing the product, it was purified by dissolving in hot acetone, running a clarification filtration over filter aid on a small Hirsch funnel, and diluting the filtrate with water to incipient crystallization. The recovery of oven-dried product, melting at 221°–222° C, was 96.5%.

Solutions of the product from acetone, ethanol, or isopropylbiphenyl gave red colors on paper coated with kaolinphenolic resins mix or with Silton clay. The colors were copiable with the Xerox 2400 copier.

Analysis: Calculated for $C_{30}H_{28}N_2O_3$: C, 77.56; H, 6.08; N, 6.03. Found: C, 77.34; H, 6.20; N, 5.85.

The IR spectrum from KBr pellet showed a strong absorbance band at 1770 cm$^{-1}$, a stretch frequency characteristic of the lactone carbonyl group.

EXAMPLE 3

Preparation of 2-amino-6-dimethylaminofluoran intermediate

A mixture of 17.1 g. (0.06 mole) of 2-(4'-dimethylamino-2'-hydroxybenzoyl)benzoic acid and 9.08 g. (0.06 mole) of p-acetamidophenol in 120 g. of concentrated sulfuric acid (reagent grade) was cooled and poured gradually as a thin stream into 700 g. ice-water under vigorous mechanical agitation, and stirred for an additional thirty minutes to ensure drowning (dilution) of all sulfuric acid droplets or pockets.

The reaction mix was brought to pH 8 (meter) by means of a 20% solution of sodium hydroxide, added gradually from dropping funnel under vigorous agitation, filtered, washed with water and dried. The yield of crude product, melting at 209° C, was 17.88 g. (83% of theory).

The product was recrystallized from a large volume of acetone, filtering off some insolubles, and diluting the filtrate with water to initiation of crystallization. The recovery of product, melting at 241° C, was 51.3% of theory. Solutions of the product from organic solvents as acetone or chloroform yielded wine red colors on electron-acceptor sheets, such as paper coated with Silton clay and kaolin phenolic resin mix.

Analysis: Calculated for $C_{22}H_{18}N_2O_3$: C, 73.73; H, 5.06; N, 7.82. Found C, 73.66; H, 5.23; N, 7.55.

The IR spectrum is similar to that of the diethylamino homolog of Example 1. The compound shows a strong band at 5.72$\mu$(=1760 cm$^{-1}$), characteristic of the lactone carbonyl group.

EXAMPLE 4

Preparation of 6-dimethylamino-2-(2'',5''-dimethylpyrryl)fluoran (Formula XI)

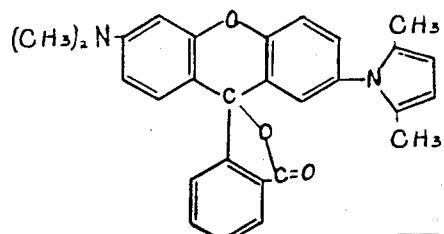

A mixture of 10.75 g. (0.03 mole) of 2-amino-6-diethylaminofluoran, 3.59 g. (0.0305 mole) of acetonylacetone, 0.5 ml. of glacial acetic acid and 30.0 ml. of anhydrous ethanol was refluxed with stirring under anhydrous conditions for about 1.5 hours, cooled in a refrigerator overnight, filtered, and the filter cake washed with cold methanol. The yield of dried product was 12.0 g. (91.7% of theory). The melting point was 257°–258° C.

The product from solutions of organic solvents, such as acetone, chloroform, etc. yields red colors on paper coated with kaolin-phenolic resin mix and Silton clay as well as with various other electron-acceptor materials. These colors are copiable with an electrostatic copier, such as the Xerox 2400 copier.

Analysis: Calculated for $C_{28}H_{24}N_2O_3$: C, 77.05; H, 5.54; N, 6.42. Found: C, 77.05; H, 5.39; N, 6.58.

The spectrum is similar to that of the diethylamino homolog. There is a strong band at 5.68μ(-1760 cm⁻¹), characteristic of the lactone carbonyl group.

EXAMPLE 5

Preparation of 2-amino-6-dimethylamino-4' or 5'-methylfluoran intermediate

An equimolar mix of 11.05 g. (0.037 mole) of 2-(4'-dimethylamino-2'hydroxybenzoyl)-4 or 5-methylbenzoic acid and 5.6 g. (0.037 mole) of p-acetamidophenol was stirred in 74 g. of reagent grade, conc. sulfuric acid at 85° C for 3.5 hours, cooled to −10° C, drowned in 430 g. ice-water and stirred for ½ hour. The drowned mix was brought to pH 8.4 by means of 20% aqueous sodium hydroxide, stirred for 1 hour, and allowed to settle overnight. The supernatant liquid was decanted and discarded. The residue was filtered on a Buchner funnel, reslurried in water, filtered and washed with water on the Buchner funnel. The yield of dried, crude product, melting at 159°–175° C, was 12.12 g. (88.4% of theory).

A 3.35 g. sample of the crude product was purified by dissolving in 235 ml. of methanol, and filtering off 0.3 g. of a light brown insoluble product. The filtrate was diluted with 322 ml. of water from a burette by gradual addition over a two-hour period. A very light brown crystalline powder, melting at 176°–180° C, was obtained in 51% recovery.

This intermediate fluoran has chromogenic properties, yielding from organic solutions wine-red colors on paper coated with Silton clay or kaolin phenolic resin mix. Analysis: Calculated for $C_{23}H_{20}N_2O_3$: C, 74.17; H, 5.41; N, 7.52. Found: C, 73.95; H, 5.52; N, 7.36.

The IR spectrum from KBr pellets showed a strong absorbance band at 3400 cm⁻¹ indicative of the NH frequency of the primary amine, and a strong absorbance band at 1755 cm⁻¹, characteristic of lactone carbonyl.

EXAMPLE 6

Preparation of 6-dimethylamino-2-(2'',5''-dimethylpyrryl)-4'(or 5')-methylfluoran(Formula XII)

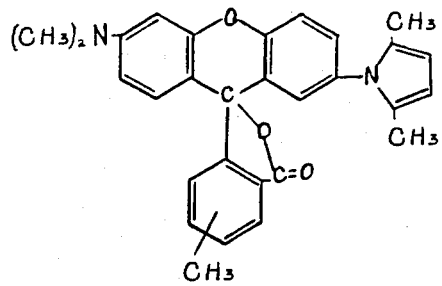

A mixture of 3.1 g. (0.0083 mole) of 2-amino-6-dimethylamino 4'(or 5')-methylfluoran prepared in Example 5 and 0.95 g. (0.0083 mole) of 97% acetonylacetone in 8.1 ml. anhydrous ethanol containing 0.2 ml. glacial acetic acid was stirred with reflux for 1.5 hours, cooled overnight at −7° C, and filered on a Hirsch funnel. The product was washed with cold methanol. The product, melting at 206°–207° C with softening from 203° C, was obtained in a yield of 2.9 g. (89.6% of theory). The product may be further purified by dissolving in hot acetone, filtering off a minute amount of insolubles and allowing the filtrate to evaporate to dryness. A 75% recovery is effected.

Solutions of the product in acetone, ethanol, benzene or isopropylbiphenyl yield red colors on Silton clay or kaolin-phenolic resin mix coated paper sheets.

Analysis: Calculated for $C_{29}H_{26}N_2O_3$: C, 77.31; H, 5.82; N, 6.22. Found: C, 77.29; H, 5.96; N, 6.08.

The IR spectrum from KBr showed a strong band at 1760 cm⁻¹, characteristic of the lactone carbonyl stretch frequency.

EXAMPLE 7

Preparation of 6-diethylamino-2-(2'',5''-dimethylpyrryl)-4-methylfluoran(Formula XIII)

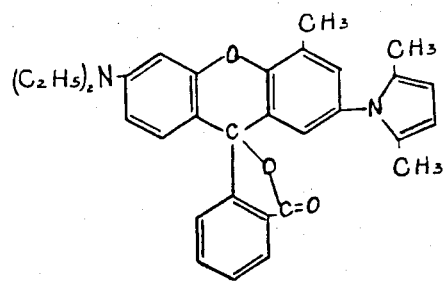

This product may be prepared conveniently from the reaction of equimolar quantities of 2-amino-6-diethylamino-4-methylfluoran and acetonylacetone in the manner described for Example 2. The intermediate, 2-amino-6-diethylamino-4-methylfluoran, is reported as 3-diethylamino-5-methyl-7-aminofluoran in U.S. Pat. No. 3,824,119.

EXAMPLE 8

Preparation of 3-chloro-6-diethylamino-2-(2'',5''-dimethylpyrryl)-fluoran (Formula XIV)

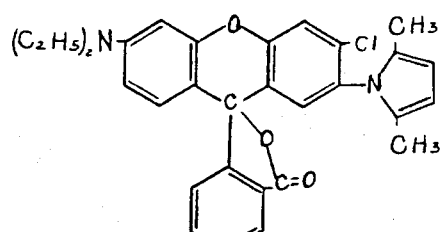

This product may be prepared according to the procedure used for Example 2, except that the 2-amino-6-diethylaminofluoran is replaced by an equivalent amount of 2-amino-3-chloro-6-diethylaminofluoran. The latter is referred to as 3-diethylamino-6-chloro-7-aminofluoran in U.S. Pat. No. 3,824,119.

Oil solutions of the pyrrylfluoran compounds of this invention, either alone or with other color formers, may readily be encapsulated by a variety of methods, as for example, the method described in U.S Pat. No. 2,800,457.

A pressure-sensitive copy paper was prepared as follows:

6-diethylamino-2-(2'',5''-dimethylpyrryl)fluoran made by the process of Example 2 was dissolved in isopropylbiphenyl at the rate of 5 g. of the fluoran to 107.5 g. of isopropylbiphenyl. This oily solution was microencapsulated in gelatin capsules and the resulting dispersion of microcapsules was coated on 15-pound bond paper with a Mayer Bar to deliver a capsule coat weight of 2.75 lbs. per 3300 sq. ft. of paper. These microcapsule coated sheets when typed against kaolin-phenolic resin mix or phenolic resin coated paper sheets showed bright red images that were copiable on the Xerox copier.

I claim:

1. A pyrrylfluoran compound represented by the general formula

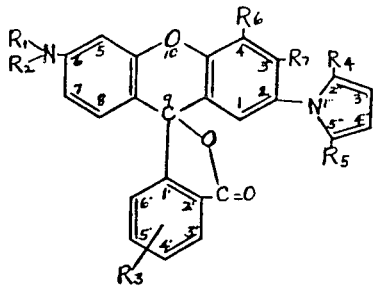

wherein, $R_1$ and $R_2$ may be the same or different and each represents hydrogen or a lower alkyl group containing one to four carbon atoms, $R_3$ is hydrogen or a methyl group, $R_4$ and $R_5$ each represent a methyl or ethyl group, and $R_6$ and $R_7$ each represents hydrogen, a methyl or ethyl group or chlorine.

2. The compound of claim 1 wherein said compound is 6-diethylamino-2-(2'',5''-dimethylpyrryl)fluoran.

3. The compound of claim 1 wherein said compound is 6-dimethylamino-2-(2'',5''-dimethylpyrryl)fluoran.

4. The compound of claim 1 wherein said compound is 6-dimethylamino-2-(2'',5''-dimethylpyrryl)4'-(or-5')-methylfluoran.

5. The compound of claim 1 wherein said compound is 6-diethylamino-2-(2'',5''-dimethylpyrryl)-4-methylfluoran.

6. The compound of claim 1 wherein said compound is 3-chloro-6-diethylamino-2-(2'',5''-dimethylpyrryl)fluoran.

7. A fluoran compound according to claim 1 in its resonance dye forms.

8. A pressure sensitive copying paper comprising a paper having coated thereon pressure rupturable gelatin microcapsules containing an organic solvent solution of a substantially colorless pyrrylfluoran compound represented by the following formula:

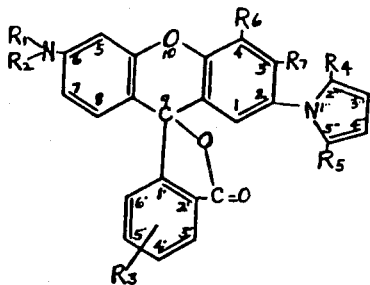

wherein, $R_1$ and $R_2$ may be same or different and each represents hydrogen or a lower alkyl group containing one to four carbon atoms, $R_3$ is hydrogen or a methyl group, $R_4$ and $R_5$ each represent hydrogen, a methyl or ethyl group or chlorine, said organic solvent solution of said substantially colorless pyrrylfluoran compounds being capable of forming a colored dye in contact with an electron acceptor.

* * * * *